United States Patent [19]

Linhart et al.

[11] 4,115,652

[45] Sep. 19, 1978

[54] PROCESS FOR THE PREPARATION OF AMINO-NITROPHENOLS

[75] Inventors: Karl Linhart; Adolf Friedrich, both of Leverkusen, Germany

[73] Assignee: Bayer Aktiengesellschaft, Leverkusen, Germany

[21] Appl. No.: 783,036

[22] Filed: Mar. 30, 1977

[30] Foreign Application Priority Data

Apr. 6, 1976 [DE] Fed. Rep. of Germany ....... 2624825

[51] Int. Cl.$^2$ .................. C07C 79/28; C07C 91/34
[52] U.S. Cl. .................................. 568/706; 260/575
[58] Field of Search .......... 260/621 M, 621 N, 622 R, 260/622 P, 575, 580

[56] References Cited

U.S. PATENT DOCUMENTS 2,464,194   3/1949   Zimmerman .................. 260/575

OTHER PUBLICATIONS

Organic Synthesis, vol. 25, pp. 5-7 (1945).

*Primary Examiner*—James O. Thomas
*Assistant Examiner*—Werren B. Lone
*Attorney, Agent, or Firm*—Burgess, Dinklage & Sprung

[57] ABSTRACT

A process for the preparation of an amino-nitro-phenol by partial reduction of a polynitrophenol by contacting the polynitrophenol with an aqueous ammonia solution and a sulfide ion, the ammonia being present in an amount of 1 to 8 mols ammonia per mol of polynitrophenol and the sulfide being present in an amount of 2.5 to 6 mols sulfide ion per mol polynitrophenol, the process being conducted at a temperature of from room temperature to 100° C.

13 Claims, No Drawings

PROCESS FOR THE PREPARATION OF AMINO-NITROPHENOLS

The present invention relates to a process for the preparation of amino-nitrophenols by means of partial reduction of polynitrophenols.

It has already been disclosed that polynitrophenols can be partially reduced by electrolysis (Report 41, 3187 (1908)) and by using sulphur dioxide in the presence of iron borings (German Patent Specification 289,454).

Furthermore, processes for the partial reduction of polynitrophenols have been disclosed, in which alkali metal sulphides or polysulphides are used as reducing agents. In Organic Synthesis 25, 5 (1945) a process is described in which 2,4-dinitrophenol is reduced to 2-amino-4-nitrophenol with sodium sulphide in a watery ammoniacal solution with the addition of ammonium chloride. Besides obtaining only moderate yields (58% to 61% of the theoretical) recovery of a sufficiently pure product can only be achieved by additional recrystallisation. Further disadvantages of this process include the very high dilution of the reaction mixture, which requires a large reaction volume, and the large quantities of ammonium chloride which have to be added for the propose of buffering.

In another process (Recueil de Travaux Chimiques des Pays-Bas 65, 358 (1946)) 2,4-dinitrophenol is reduced with sodium disulphide in ethanol in the presence of caustic soda solution.

In this, however, both monoisomers result, which have to be separated from each other by a complicated extraction process using ether.

In the U.S. Patent Specification No. 2,464,194 a process is described for the partial reduction of 2,4-dinitrophenol and 6-chloro-2,4-dinitrophenol using alkali metal sulphides or polysulphides, in which the phenols are first of all converted to alkaline earth phenolates and are separated as such. Apart from the long reaction times of the reduction the very high dilutions required in this process are very disadvantageous from an economical point of view.

What is particularly difficult is the partial reduction of 2,4-dinitrophenols according to methods already disclosed, when the starting product is not pure dinitrophenol, but a waste product contaminated with organic by-products, since the impurities obstruct to a certain extent the partial reduction and produce large quantities of by-products, which can only be separated with difficulty.

It has now been found that one can produce amino-nitrophenols in a technically advantageous manner by means of partial reduction from the corresponding polynitrophenols, if the reduction is conducted in an aqueous solution with 1 to 8 mols ammonia to 1 mol polynitrophenol in the presence of 2.5 to 6 mols sulphide ions per mol polynitrophenol within a temperature range of from room temperature to 100° C.

A preferred embodiment of the process of the invention is the embodiment of an aqueous solution such that the ratio of mols of polynitrophenol to mols of ammonia is 1:1 to 1:4. It is particularly advantageous if 1.9 to 2.1 mols ammonia are used per mol of the polynitrophenol.

Furthermore, it is advantageous for the process according to the invention if 2.5 to 4 mols sulphide ions are employed per mol polynitrophenol for the reduction process. Of particular preference for this are approx. 3 to 3.2 mols sulphide ions per mol polynitrophenol.

A temperature range of 40° to 90° C. proved advantageous for the reduction of the polynitrophenols, a range of 60° to 80° C. being particularly advantageous.

The sulphides, polysulphides and/or hydrogen sulphides of the elements of the first and second main group of the periodic table can be used in the process, for example, the sulphides, polysulphides and/or hydrogen sulphides of the elements lithium, sodium, potassium, rubidium, caesium, magnesium, calcium, strontium, barium.

Sodium, potassium, calcium and/or ammonium sulphide, as well as sodium, potassium, calcium and/or ammonium hydrogen sulphide are preferably employed in the process according to the invention. Compounds of the formula

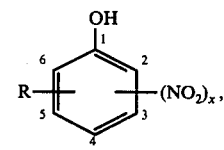

can be used as the polynitrophenol for the process according to the invention, wherein x signifies the numbers 2 or 3 and R stands for hydrogen, alkyl, halogen, alkoxy, aryl or aralkyl, or represents a sulphonic acid or carboxylic acid residue, which can also be present in the form of their amides or esters.

Hydrocarbon residues, for example, with up to 12 C atoms can be considered for use as residues R, e.g. alkyl residues, such as methyl, ethyl, n-propyl, isopropyl, n-butyl, isobutyl, tertiary butyl, n-pentyl, iso-pentyl, 2-methyl pentyl, 3-methyl pentyl, n-octyl, iso-octyl as well as cyclohexyl; aryl residues, such as phenyl, naphthyl; aralkyl residues, such as benzyl, phenyl ethyl, phenyl propyl, phenyl butyl; alkoxy residues, such as methoxy or ethoxy the terms "residue" or "residues" as used herein is synonymous with the the term "radical" or "radicals".

Compounds of the above formula are preferred in which R stands for hydrogen, lower alkyl with up to 4 C atoms, fluorine, chlorine, bromine or a sulphonic or carboxylic acid residue.

The nitro groups are situated for example in the 2,4 or 2,5 or 2,6 or 3,5 or 2,4,6 position.

The substituents R are generally situated in the 3 or 4 or 5 or 6 position.

The following can for example be named as compounds corresponding with the formula: 2,4-dinitro phenol; 2,5-dinitro phenol; 2,6-dinitro phenol; 2,4,6-trinitro phenol; 6-chloro-2,4-dinitro phenol; 4-chloro-2,6-dinitro phenol; 2,4-dinitro phenol-6-sulphonic acid; 2,4-dinitrophenol-5-sulphonic acid; 3,5-dinitro-2-hydroxy-toluene; 3,5-dinitro-2-hydroxy-benzoic acid; 3,5-dinitro-4-hydroxy-benzoic acid.

In the process according to the invention 2,4- and 2,6-dinitrophenol are employed with particular preference, as well as derivatives of the 2,4- and 2,6-dinitrophenol, especially those which are substituted by chlorine or a sulpho group, e.g. 4-chloro-2,6-dinitrophenol.

Furthermore contaminated polynitro phenols can be used for the partial reduction in the process according to the invention, e.g. contaminated 2,4-dinitro phenol, whose impurities consist essentially of other phenol derivatives and condensed aromatic compounds. For example a moist 2,4-dinitro phenol is used, which contains approx. 10% of the above-mentioned impurities.

The contaminated polynitrophenols are obtained as by-products during the production of anthraquinone dyestuffs. The polynitrophenols are essentially contaminated with 1,8-dihydroxy-4,5-dinitro-anthraquinone, 1,5-dihydroxy-4,8-dinitro-anthraquinone, 1,4-dinitro-5,8-dihydroxyanthraquinone, 1,6-dinitrophenol, 1,5-dinitrophenol, mononitrophenols and phenol. In particular the impurities consist of 1,8-dihydroxy-4,5-dinitroanthraquinone and/or 1,5-dihydroxy-4,8-dinitroanthraquinone.

According to the process according to the invention the reduction takes place in about 1 to 10 hours at a temperature of approx. 20 to 100° C. Preferably the sulphide, in the form of an aqueous solution is continually fed into a reaction mixture containing ammonia, water (ammonium hydroxide) and polynitrophenol within ½ to 3 hours at a temperature range of 60° to 90° C. It is particularly advantageous to introduce an aqueous sodium hydrogen sulphide solution at a temperature of about 80° C. The working up process can be conducted in the following manner.

Following the reduction the monoaminonitrophenol is precipitated in the form of its salt by cooling to the temperature range of 0° to 60° C. It is filtered off, dissolved in water and by bringing the solution to a suitable pH value, for example within the range of 0 to 7, is precipitated as a phenol derivative. Also, by adding sufficient amounts of acid the monoaminonitrophenol can be brought into a solution as an acid salt, filtered for the purpose of further purification and then brought to a suitable pH value, for example within the range of 0 to 7, by using a lye solution, the phenol derivative again being precipitated. A further method of working up the reaction mixture consists of first of all filtering it whilst hot, isolating the salt from the filtrate by cooling and then proceeding according to one of the two above-described processes.

The purity of the products as determined by polarography is greater than 98%.

The process according to the invention is particularly distinguished in that the aminonitrophenols are recovered in high yields and degrees of purity, while the reaction volumes are kept low and the addition of buffering substances is not necessary.

The amino nitro phenols produced according to the process of the invention are valuable intermediate products for the preparation of, for example, dyes (Grundlegende Operation der Farbenchemie, Fierz-David u. Blangey, Wien 1952).

The parts as mentioned in the following examples signify parts by weight, henceforth represented by the letter 'p', and the percentages signify percentages by weight.

EXAMPLE 1

An amount corresponding to 184 p 2,4-dinitrophenol of a contaminated 2,4-dinitrophenol is heated to 80° C. with 150 p water and 136 p 25% strength aqueous ammonia solution. 487.5 p of a 35.4% strength aqueous sodium hydrogen sulphide solution are fed into the suspension at 80° C. within 2 hours. Then the reaction mixture, filtered, if necessary, whilst hot, is cooled to 20° C. The salt of the 2-amino-4-nitrophenol is thereby precipitated in a well-crystallised form. It is isolated by filtration. The filtercake is fed into a mixture of 200 p water and 218 p 30% strength salicic acid. The mixture can then be heated to 50° C. and filtered. The 2-amino-4-nitrophenol is precipitated from the filtrate by bringing it to a pH value of between 3 and 4. After drying 114-118 p, corresponding to 74 to 76% of the theoretical, are recovered, based on the 2-amino-4-nitrophenol used as starting material; the purity of the yield is > 99%. Melting-point: 144° to 145° C.

EXAMPLE 2

If one proceeds as described in Example 1, but uses instead of the sodium hydrogen sulphide solution 524 p of a 40% strength ammonium sulphide solution, the product as described in Example 1 is recovered in the same yield and in a 98% pure form. Melting-point: 144° C.

EXAMPLE 3

218.5 p 2,4-dinitro-6-chlorophenol are heated to 80° C. with 500 p water and 136 p of a 25% strength aqueous ammonia solution. 487.5 p of a 35.4% strength aqueous sodium hydrogen sulphide solution are fed into the suspension at 80° C. within 40 minutes. 15 p common salt are added and the mixture is cooled to room temperature. The precipitated well-crystallised salt is separated off. The filtercake is fed into a mixture of 260 p 30% strength salicic acid and 1000 p water. The mixture is heated to 80° C. and filtered. From the filtrate the 2-amino-4-nitro-6-chlorophenol is precipitated by bringing it to a pH value of 3.5. After drying 135–140 p 2-amino-4-nitro-6-chlorophenol, corresponding to 71 to 74% of the theoretical based on the starting product used, are obtained and in a >99% pure form.

EXAMPLE 4

If one proceeds as described in Example 3, but uses instead of the 2,4-dinitro-6-chloro-phenol 218.5 p 4-chloro-2,6-dinitrophenol the 4-chloro-6-nitro-2-aminophenol is recovered in a yield of 73 to 76% of the theoretical based on the starting product used and in a >98% pure form.

What is claimed is:

1. A process for preparing an amino-nitrophenol which consists essentially of contacting a polynitrophenol of the formula

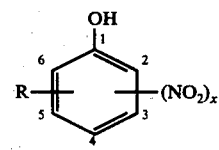

wherein
  x signifies the number 2 and R stands for low alkyl, fluorine, chlorine, bromine or carboxylic or sulfonic acid residue with a reaction mixture consisting essentially of an aqueous ammonia solution and sodium hydrogen sulfide, said aqueous ammonia being present in an amount of 1 to 8 mols ammonia per mol of polynitrophenol and said sodium hydrogen sulfide being present in an amount of 2.5 to 6 mols sulfide ion per mol of polynitrophenol and the reaction being performed at room temperature up to 100° C.

2. A process according to claim 1 wherein the polynitrophenol is contacted with 1 to 4 mols ammonia and 2.5 to 4 mols sulfide ions per mol polynitrophenol.

3. A process according to claim 1 wherein the polynitrophenol is contacted with 1.9 to 2.1 mols ammonia and 3 to 3.2 mols sulfide ion per mol of polynitrophenol.

4. A process according to claim 1 wherein the polynitrophenol is contacted with the ammonia and sulfide ions at a temperature in the range of 60° to 80° C. for between 1 and 10 hours by continually introducing the sulfide in the form of an aqueous solution into an aqueous solution containing said ammonia and said polynitrophenol.

5. A process according to claim 1 wherein the reaction is conducted at 80° C. within 2.5 hours.

6. A process according to claim 1 wherein the sulfide is in the form of its ammonium salt or a salt of an element of the first or second main group of the periodic table.

7. A process according to claim 1 wherein the sulfide ion is in the form of its acid salt.

8. A process according to claim 1 wherein the polynitrophenol is 2,4-dinitrophenol or 2,6-dinitrophenol.

9. A process according to claim 1 wherein the polynitrophenol is 2,4 and/or 2,6-dinitrophenol substituted by a chloro or sulfo group.

10. A process according to claim 1 wherein the polynitrophenol is contaminated 2,4-dinitrophenol.

11. A process according to claim 1 wherein the resultant monoamino-nitrophenol is precipitated in the form of its salt, the salt is dissolved in water to convert the amino-nitrophenolate into amino-nitrophenol and the solution is brought to a pH of 0 to 7.

12. A process according to claim 1 wherein the resultant amino-nitrophenol from the partial reduction is formed into an acid salt in the reaction mixture and after filtration it is dissolved in water at a pH of 0 to 7 and amino-nitrophenol is precipitated therefrom.

13. A process according to claim 1 wherein the reaction mixture is filtered following the partial reduction, the amino-nitrophenolate is isolated from the filtrate by cooling and amino-nitrophenolate is converted into amino-nitrophenol.

* * * * *